(12) United States Patent
Bosanac et al.

(10) Patent No.: US 8,940,893 B2
(45) Date of Patent: Jan. 27, 2015

(54) HETEROAROMATIC COMPOUNDS AS BTK INHIBITORS

(71) Applicants: Todd Bosanac, New Milford, CT (US);
Darren Disalvo, New Milford, CT (US);
Joshua Courtney Horan, Danbury, CT (US); Shuang Liang, Danbury, CT (US);
Renee M. Zindell, New Milford, CT (US)

(72) Inventors: Todd Bosanac, New Milford, CT (US);
Darren Disalvo, New Milford, CT (US);
Joshua Courtney Horan, Danbury, CT (US); Shuang Liang, Danbury, CT (US);
Renee M. Zindell, New Milford, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/210,517

(22) Filed: Mar. 14, 2014

(65) Prior Publication Data

US 2014/0275014 A1 Sep. 18, 2014

Related U.S. Application Data

(60) Provisional application No. 61/787,596, filed on Mar. 15, 2013.

(51) Int. Cl.
| | |
|---|---|
| *C07D 487/04* | (2006.01) |
| *C07D 401/14* | (2006.01) |
| *C07D 403/04* | (2006.01) |
| *C07D 403/10* | (2006.01) |
| *C07D 403/14* | (2006.01) |
| *A61K 31/519* | (2006.01) |
| *A61K 31/4427* | (2006.01) |
| *A61K 31/397* | (2006.01) |
| *A61P 19/02* | (2006.01) |

(52) U.S. Cl.
CPC .................................. *C07D 487/04* (2013.01)
USPC ...... 544/262; 544/256; 514/262.1; 514/258.1

(58) Field of Classification Search
CPC .. C07D 487/04; C07D 403/10; C07D 403/14; C07D 401/14; A61K 31/519
USPC ..................... 544/256, 262; 514/258.1, 262.1
See application file for complete search history.

(56) References Cited

U.S. PATENT DOCUMENTS

| | | |
|---|---|---|
| 8,377,946 B1 | 2/2013 | Chen et al. |
| 8,557,803 B2 | 10/2013 | Yamamoto et al. |
| 2008/0076921 A1 | 3/2008 | Honigberg et al. |

FOREIGN PATENT DOCUMENTS

| | | |
|---|---|---|
| CA | 2784647 A1 | 7/2011 |
| EP | 2543375 A1 | 1/2013 |
| WO | 2007117692 A2 | 10/2007 |
| WO | 2008121742 A2 | 10/2008 |
| WO | 201012690 A1 | 2/2010 |
| WO | 2010055304 A2 | 5/2010 |
| WO | 2011082732 A1 | 7/2011 |
| WO | 2011152351 A1 | 12/2011 |
| WO | 2013113097 A1 | 8/2013 |
| WO | 2014025976 A1 | 2/2014 |
| WO | 2014068527 A1 | 5/2014 |
| WO | 2014082598 A1 | 6/2014 |

OTHER PUBLICATIONS

Whang et al., Drug Discovery Today, pp. 1-5, 2014.*
Akinleye et al. Journal of Hematology & Oncology 2013, 6:59.*
Chakravarty et al. Clinical Immunology (2013) 148, 66-78.*
Abstract in English for WO 2011/082732, publication date Jul. 14, 2011.
International Search Report and Written Opinion for PCT/US2013/054096 mailed Sep. 30, 2013.
International Search Report and Written Opinion for PCT/US2014/026113, mailing date Jun. 2, 2014.
International Search Report and Written Opinion for PCT/US2014/026966, mailing date Jul. 22, 2014.
Summary of Pfizer Oral Presentation, "Targeted covalent reversible inhibitors for Bruton's Tyrosine Kinase." Presented by Suvit Thaisrivongs on Apr. 16, 2013.

* cited by examiner

*Primary Examiner* — Venkataraman Balasubramanian
(74) *Attorney, Agent, or Firm* — Michael P. Morris; Anthony P. Bottino

(57) ABSTRACT

The present invention encompasses compounds of the formula (I)

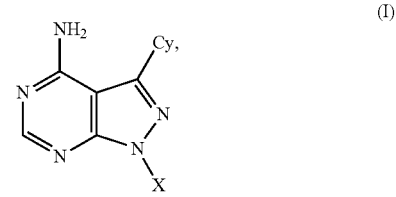

wherein the groups X and Cy are defined herein, which are suitable for the treatment of diseases related to BTK, process of making, pharmaceutical preparations which contain compounds and their methods of use.

10 Claims, No Drawings

HETEROAROMATIC COMPOUNDS AS BTK INHIBITORS

BACKGROUND OF THE INVENTION

1. Technical Field

The present invention relates to novel compounds which inhibit BTK and their use as medicaments.

2. Background Information

Members of the protein kinase family of human enzymes play important regulatory roles in a multitude of distinct signal transduction processes due to their post-translational modification of specific proteins via the addition of a phosphate group (Hunter, *Cell,* 1987 50, 823-829). Bruton's tyrosine kinase (BTK) is a member of the Tec family of tyrosine kinases and plays a criticial role in B cell development, activation and antibody production.

The contribution of BTK to B cell biology is exemplified in the X-linked agammaglobulinemia (XLA) immunodeficiency in humans (reviewed in Lindvall, Immunol Rev 2005, 203, 200-xxx) that display attenuated calcium signaling upon BCR engagement, lack mature B cells in periphery due to block between pro- and pre-B cells stage and have lower levels of circulating antibodies than normal healthy subjects. The outcome of recent clinical trials with B cell depleting anti-CD20 molecules in diseases such as rheumatoid arthritis (RA) and multiple sclerosis (MS) support the hypothesis that B cells offer an important intervention node for controlling autoimmune disorders (Townsend et al. 2010). As such, attenuation of B cell activation and proliferation via inhibition of BTK may offer similar therapeutic benefit and is consistent with the demonstrated resistance of BTK-deficient mice to collagen induced arthritis (Jansson, 1993, Clin Exp Immunol 94, 459-xxx) and experimental autoimmune encephalitis (Svensson et al. 2002 and Mangla et al 2004). Similarly, the clinical efficacy observed with a neutralizing antibody to the B cell stimulating factor BlyS supports a role for B cells in the pathophysiology of systemic lupus erythematosus (SLE) (La Cava 2010). Given the necessity for BTK for the production of autoantibodies, including anti-DNA antibodies, in murine models of SLE (Steinberg et al., 1982; Golding et al., 1983; Scribner et al., 1987; Seldin et al., 1987; Satterthwaite et al., 1998; Takeshita et al., 1998; Whyburn et. al., 2003), BTK inhibitors may offer therapeutic benefit to SLE patients.

Within myeloid cells, BTK signal transduction is necessary for the stimulated release of inflammatory cytokines such as TNF from stimulated monocytes (Horwood, J Exp Med, 2003, 1603-xxx) and for optimal actin cytoskeletal organization and lacunar bone resorption in isolated osteoclasts (Danks, 2011, J Bone and Mineral Research, 26, 182-192). Bone marrow derived mast cells lacking BTK exhibit impaired activation-induced degranulation and cytokine release (ref). Given the role of BTK in signal transduction processes across multiple cell types implicated in the pathogenesis of autoimmune and allergic disorders, inhibition of BTK activity may provide clinical benefit in diseases such as RA, MS, SLE, asthma and allergic disorders.

SUMMARY OF THE INVENTION

The invention comprises a novel class of heteroaromatic compounds and methods for making and using the same. These compounds are useful for the treatment of autoimmune and allergic disorders in that they exhibit good inhibitory effect upon BTK.

DETAILED DESCRIPTION OF THE INVENTION

In a first generic embodiment, there is provided a compound of the formula (I)

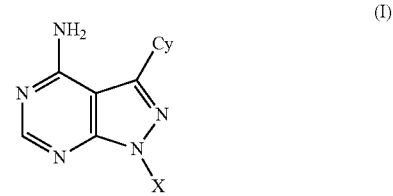

Cy is carbocycle, heteroaryl or heterocycle, each is substituted by $R_1$ and optionally substituted by halogen, halo $C_{1-4}$ alkyl, $C_{1-4}$ alkyl, oxo and $C_{1-4}$ alkoxy;

$R_1$ is chosen from:

L-Ar, $C_{1-6}$ alkyl, $-S(O)_m-R_3$ and $C_{1-6}$ alkoxy, each Ar, $C_{1-6}$ alkyl and $C_{1-6}$ alkoxy are optionally substituted by benzyl, halogen, halo $C_{1-4}$ alkyl, $C_{1-4}$ alkyl, $R_2-S(O)_m-$, $-CN$, $-C(O)-N(R_3)_2$ or $C_{1-4}$ alkoxy;

L is a linker chosen from a bond, O, >C(O), $-(CH_2)_n-$, $-O-(CH_2)_n-$, $-N(R_3)-$, $-N(R_3)-(CH_2)_n$, $-(CH_2)_n-N(R_3)-$, $-C(O)-N(R_3)-$, $-C(O)-N(R_3)-(CH_2)_n-$, $-N(R_3)-C(O)-N(R_3)-$, $-N(R_3)-C(O)-$, $-S(O)_m-N(R_3)-$, $R_3-S(O)_m-$, and $-N(R_3)-S(O)_m-$, wherein the $-CH_2-$ in each L can have 1-2 hydrogens replaced by $C_{1-3}$ alkyl, said $C_{1-3}$ alkyl groups can optionally cyclize to form a $C_{3-6}$ cycloalkyl ring;

Ar is carbocycle, heterocycle or heteroaryl;

X of the formula (I) is a nitrogen containing $C_6$-$C_{10}$ spirocycle, each X is substituted by one $R_4$ and optionally substituted by halogen, halo $C_{1-4}$ alkyl, $C_{1-4}$ alkyl and $C_{1-4}$ alkoxy;

$R_4$ is

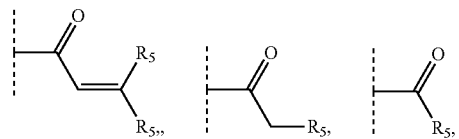

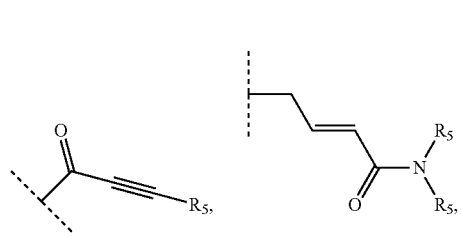

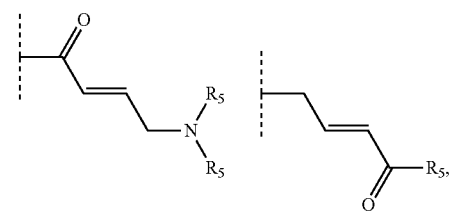

-continued

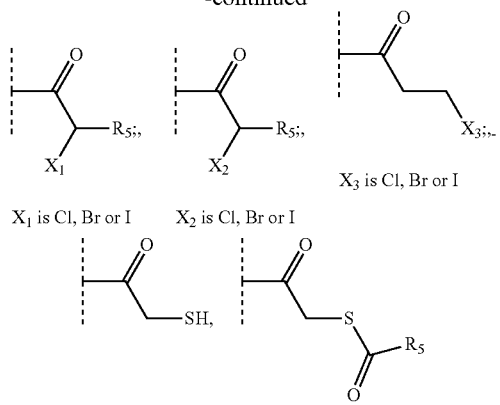

X₁ is Cl, Br or I    X₂ is Cl, Br or I    X₃ is Cl, Br or I each n is independently 1-4;
each m is independently 0-2;
each $R_2$ and $R_3$ are independently chosen from hydrogen or $C_{1-4}$ alkyl;
each $R_5$ is independently chosen from hydrogen, halogen, $C_{1-4}$ alkyl, $C_{1-4}$ alkoxy, $C_{1-4}$ alkyl$C_{1-4}$alkoxy, $C_{1-4}$ alkylhydroxy, —$(CH_2)_n$-heterocycle and heterocycle each heterocycle optionally substituted by halogen, OH or $R_2$—$S(O)_m$—;
each group defined above for Cy, $R_1$-$R_5$, and Y can be, where possible partially or fully halogenated;
or a pharmaceutically acceptable salt thereof.

In a further embodiment, there is provided a compound of the formula (I) according to any of the embodiments herein and wherein
Cy is phenyl, pyrazolyl, pyridinyl, pyrrolyl, imidazolyl, thiazolyl, furanyl, oxazolyl, isoxazolyl, thienyl, pyridazinyl, pyrimidinyl, pyrazinyl or pyranyl each is substituted by $R_1$ and optionally substituted by $C_{1-4}$ alkyl, F, Cl or oxo;
$R_1$ is chosen from:
L-Ar and —$S(O)_m$—$R_3$, each $R_1$ is optionally substituted by Br, $C_{1-4}$ alkyl, $R_3$—$S(O)_2$—, —CN, —C(O)—NH($R_3$) and $C_{1-3}$ alkoxy;
Ar is phenyl, pyridinyl, pyridazinyl, pyrimidinyl optionally substituted by benzyl, pyrazinyl, benzoxazolyl, indolyl, isoindolyl, benzofuranyl, benzimidazolyl, benzothiazolyl, piperidinyl, piperazinyl or pyrrolidinyl
or a pharmaceutically acceptable salt thereof.

In a further embodiment, there is provided a compound of the formula (I) according to any of the embodiments herein and wherein
Cy is phenyl or pyridinyl, each is substituted by $R_1$ and optionally substituted by F, Cl, oxo or $C_{1-2}$ alkoxy;
$R_1$ is L-Ar, each $R_1$ is optionally substituted by Br, $C_{1-4}$ alkyl, $CH_3$—$S(O)_2$—, —CN, —C(O)—NH($R_3$) and $C_{1-2}$ alkoxy;
Ar is phenyl, pyridinyl, pyridazinyl, pyrimidinyl optionally substituted by benzyl, pyrazinyl, benzoxazolyl, indolyl, isoindolyl, benzofuranyl, benzimidazolyl, benzothiazolyl or piperidinyl;
or a pharmaceutically acceptable salt thereof.

In a further embodiment, there is provided a compound of the formula (I) according to any of the embodiments herein and wherein
Cy is phenyl or pyridinyl, each is substituted by $R_1$ and optionally substituted by F, Cl, oxo or $C_{1-2}$ alkoxy;
L-Ar is optionally substituted by F, Cl, $C_{1-4}$ alkyl, $CH_3$—$S(O)_2$—, —CN, —C(O)—NH($CH_3$) and $C_{1-2}$ alkoxy;
Ar is phenyl or pyrimidinyl;
or a pharmaceutically acceptable salt thereof.

In a further embodiment, there is provided a compound of the formula (I) according to any of the embodiments herein and wherein
X is

or

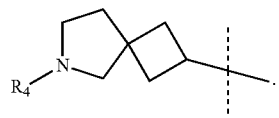

or a pharmaceutically acceptable salt thereof.

In a further embodiment, there is provided a compound of the formula (I) according to any of the embodiments herein and wherein
$R_4$ is

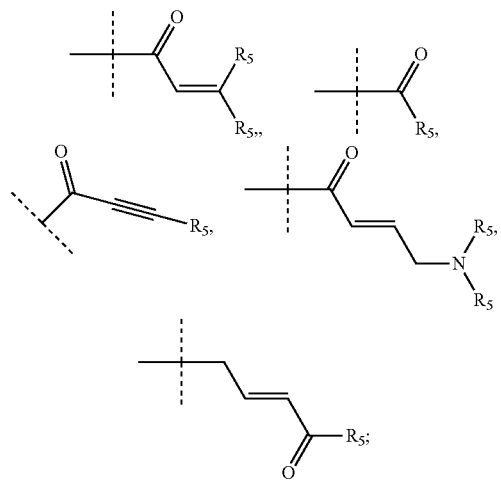

each $R_5$ is independently chosen from hydrogen, $C_{1-3}$ alkyl, halo $C_{1-3}$ alkyl, $C_{1-3}$ alkyl$C_{1-3}$ alkoxy, —$CH_2$-heterocycle and heterocycle each heterocycle optionally substituted by F, Cl, OH and $CH_3$—$S(O)_2$— and each heterocycle chosen from pyrrolidinyl, piperidinyl, morpholinyl, 1,4-oxazepane and oxirane;
or a pharmaceutically acceptable salt thereof.

In a further embodiment, there is provided a compound of the formula (I) according to any of the embodiments herein and wherein
Cy is

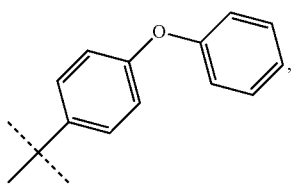

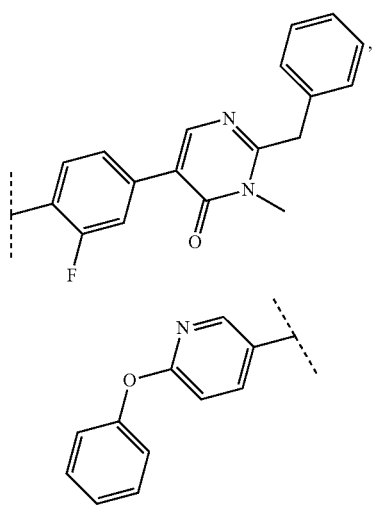

or

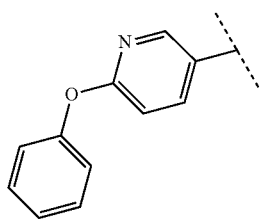

or a pharmaceutically acceptable salt thereof.

In a further embodiment, there is provided a compound of the formula (I) according to any of the embodiments herein and wherein X is

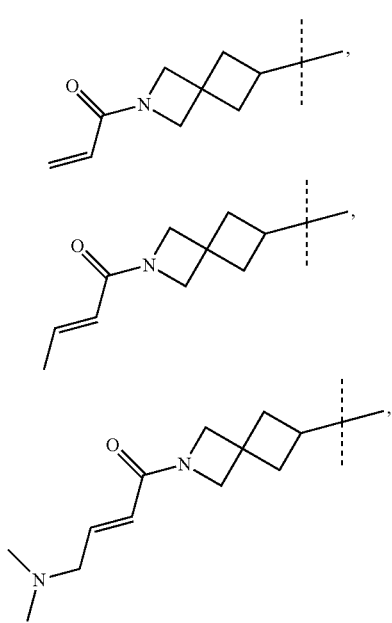

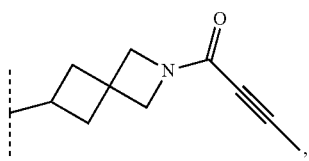

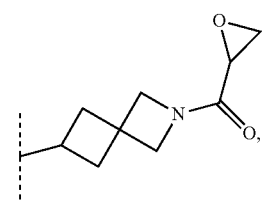

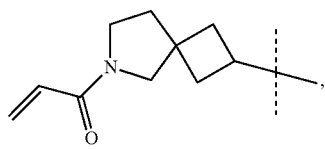

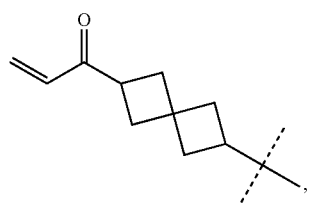

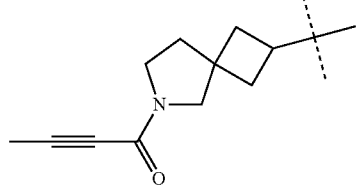

or

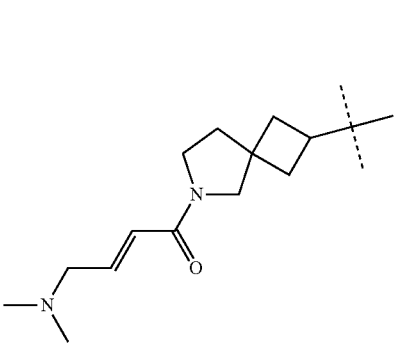

or a pharmaceutically acceptable salt thereof.

In another embodiment, the invention provides made compounds in Table I which can be made in view of the general schemes, examples and methods known in the art.

| Example # | Compound | BTK (IC50 nM) | HPLC Method | RT (min) | m/z [M + H]+ |
|---|---|---|---|---|---|
| 1 | | 1.0 | A | 0.8 | 453 |
| 2 | | 1.8 | A | 0.67 | 510.23 |
| 3 | | 0.83 | A | 0.93 | 465.19 |
| 4 | | 13 | A | 0.75 | 469.12 |
| 5 | | 0.87 | A | 0.81 | 466.9 |

Table of compounds and Biological activity

-continued

| Table of compounds and Biological activity | | | | | |
|---|---|---|---|---|---|
| Example # | Compound | BTK (IC50 nM) | HPLC Method | RT (min) | m/z [M + H]+ |
| 6 | | 0.85 | A | 1.58 | 577.35 |
| 7 | | 1.1 | A | 0.85 | 466.33 |
| 8 | | 2.4 | A | 0.8 | 454.17 |
| 9 | | 83 | A | 0.85 | 468.35 |
| 10 | | 65 | A | 0.69 | 469.61 |

-continued

Table of compounds and Biological activity

| Example # | Compound | BTK (IC50 nM) | HPLC Method | RT (min) | m/z [M + H]+ |
|---|---|---|---|---|---|
| 11 | | 1.6 | A | 0.87 | 453.51 |
| 12 | | 1.0 | A | 0.92 | 467.67 |
| 13 | | 0.74 | A | 2.07 | 480.29 |
| 14 | | 4.0 | A | 0.85 | 481.8 |

-continued

Table of compounds and Biological activity

| Example # | Compound | BTK (IC50 nM) | HPLC Method | RT (min) | m/z [M + H]+ |
|---|---|---|---|---|---|
| 15 | | 32 | A | 0.66 | 511.32 |
| 16 | | 8.1 | A | 0.52 | 525.12 |
| 17 | | 7.1 | A | 0.47 | 525.56 | or the pharmaceutically acceptable salts thereof.

The present invention further relates to metabolites, and prodrugs of compounds of the formula (I).

The present invention further relates to a pharmaceutically acceptable salt of a compound of the formula (I) with anorganic or organic acids or bases.

In another aspect the invention relates to compounds of formula (I)—or the pharmaceutically acceptable salts thereof—as medicaments.

In another aspect the invention relates to compounds of formula (I)—or the pharmaceutically acceptable salts thereof—for use in a method for treatment of a pateint.

In another aspect the invention relates to compounds of formula (I)—or the pharmaceutically acceptable salts thereof—for use in the treatment of autoimmune diseases and allergic disorders.

In another aspect the invention relates to the use of compounds of formula (I)—or the pharmaceutically acceptable salts thereof—for preparing a pharmaceutical composition for the treatment of autoimmune diseases and allergic disorders.

In another aspect the invention relates to a method for the treatment of autoimmune diseases and allergic disorders comprising administering a therapeutically effective amount of a compound of formula (I)—or one of the pharmaceutically acceptable salts thereof—to a patient.

In another aspect the invention relates to a pharmaceutical preparation containing as active substance one or more compounds of formula (I)—or the pharmaceutically acceptable salts thereof—optionally in combination with conventional excipients and/or carriers.

Definitions

Terms that are not specifically defined here have the meanings that are apparent to the skilled man in the light of the overall disclosure and the context as a whole.

As used herein, the following definitions apply, unless stated otherwise:

The use of the prefix $C_{x-y}$, wherein x and y each represent a natural number, indicates that the chain or ring structure or combination of chain and ring structure as a whole, specified and mentioned in direct association, may consist of a maximum of y and a minimum of x carbon atoms.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

For example, the term "$C_{1-5}$alkyl" includes for example H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

Further examples of alkyl are methyl (Me; —CH$_3$), ethyl (Et; —CH$_2$CH$_3$), 1-propyl (n-propyl; n-Pr; —CH$_2$CH$_2$CH$_3$), 2-propyl (i-Pr; iso-propyl; —CH(CH$_3$)$_2$), 1-butyl (n-butyl; n-Bu; CH$_2$CH$_2$CH$_2$CH$_3$), 2-methyl-1-propyl (iso-butyl; i-Bu; —CH$_2$CH(CH$_3$)$_2$), 2-butyl (sec-butyl; sec-Bu; —CH(CH$_3$)CH$_2$CH$_3$), 2-methyl-2-propyl (tert-butyl; t-Bu; —C(CH$_3$)$_3$), 1-pentyl (n-pentyl; —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 3-methyl-1-butyl (iso-pentyl; —CH$_2$CH$_2$CH(CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 2,2-dimethyl-1-propyl (neo-pentyl; —CH$_2$C(CH$_3$)$_3$), 2-methyl-1-butyl (—CH$_2$CH(CH$_3$)CH$_2$CH$_3$), 1-hexyl (n-hexyl; —CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 2,3-dimethyl-1-butyl (—CH$_2$CH(CH$_3$)CH(CH$_3$)CH$_3$), 2,2-dimethyl-1-butyl (—CH$_2$C(CH$_3$)$_2$CH$_2$CH$_3$), 3,3-dimethyl-1-butyl (—CH$_2$CH$_2$C(CH$_3$)$_3$), 2-methyl-1-pentyl (—CH$_2$CH(CH$_3$)CH$_2$CH$_2$CH$_3$), 3-methyl-1-pentyl (—CH$_2$CH$_2$CH(CH$_3$)CH$_2$CH$_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another (combined) group such as for example $C_{x-y}$alkylamino or $C_{x-y}$alkoxy.

Unlike alkyl, alkenyl consists of at least two carbon atoms, wherein at least two adjacent carbon atoms are joined together by a C—C double bond and a carbon atom can only be part of one C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Alkenyl may optionally be present in the cis or trans or E or Z orientation with regard to the double bond(s).

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —CF$_3$, —CHF$_2$, —CH$_2$F, —CF$_2$CF$_3$, —CHFCF$_3$, —CH$_2$CF$_3$, —CF$_2$CH$_3$, —CHFCH$_3$, —CF$_2$CF$_2$CF$_3$, —CF$_2$CH$_2$CH$_3$, —CF═CF$_2$, —CCl═CH$_2$, —CBr═CH$_2$, —C≡C—CF$_3$, —CHFCH$_2$CH$_3$, —CHFCH$_2$CF$_3$ etc.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms together.

If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl.

Corresponding groups are an example:
cyclohexyl

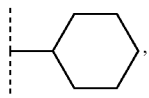

wherein the dashed line - - - - - - indicates the point of attachment.

Spirocycle is a spiro-hydrocarbon ring one carbon atom (spiroatom) belongs to two rings together.

Aryl denotes mono-, bi- or tricyclic carbocycles with at least one aromatic carbocycle. Preferably, it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be saturated or partially saturated.

If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl and naphthyl.

The above definition of aryl also applies if aryl is part of another (combined) group as for example in arylamino, aryloxy or arylalkyl.

Heterocyclyl denotes ring systems, which are derived from the previously defined cycloalkyl or spirocycle by replacing one or more of the groups —CH$_2$— independently of one another in the hydrocarbon rings by the groups —O—, —S— or —NH—, wherein a total of not more than five heteroatoms may be present, at least one carbon atom may be present between two oxygen atoms and between two sulphur atoms or between one oxygen and one sulphur atom and the ring as a whole must have chemical stability. Heteroatoms may optionally be present in all the possible oxidation stages (sulphur→sulphoxide —SO—, sulphone —SO$_2$—; nitrogen→N-oxide).

If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system.

Examples of heterocyclyl are piperidinyl, piperazinyl, pyrrolidinyl, morpholinyl, or the following heterocyclic spirocycles

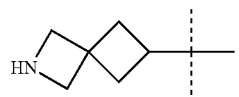

or

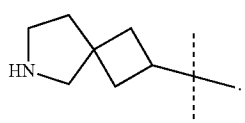

Heteroaryl denotes monocyclic heteroaromatic rings or polycyclic rings with at least one heteroaromatic ring, which compared with the corresponding aryl or cycloalkyl, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system.

If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen.

Examples of heteroaryl are pyridinyl, pyridazinyl, pyrimidinyl, pyrazinyl, benzoxazolyl, indolyl, isoindolyl, benzofuranyl, benzimidazolyl, benzothiazolyl, pyrrolyl, imidazolyl, thiazolyl, furanyl, oxazolyl, isoxazolyl, thienyl, pyranyl, and the like.

Heteroatoms may optionally be present in all the possible oxidation stages (sulphur→sulphoxide —SO—, sulphone —SO$_2$—; nitrogen→N-oxide).

Carbocycles include hydrocarbon rings containing from three to twelve carbon atoms. These carbocycles may be either aromatic either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl.

All cyclic and acyclic systems defined in this section hereinabove shall be understood to be optionally partially or fully halogenated where possible and unless otherwise indicated.

Stereochemistry/solvates/hydrates: Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof. The compounds and salts of the invention can exist in unsolvated as well as solvated forms with pharmaceutically acceptable solvents such as water, ethanol and the like. In general, the solvated forms such as hydrates are considered equivalent to the unsolvated forms for the purposes of the invention.

Salts: The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio.

As used herein "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include acetates, ascorbates, benzenesulphonates, benzoates, besylates, bicarbonates, bitartrates, bromides/hydrobromides, Ca-edetates/edetates, camsylates, carbonates, chlorides/hydrochlorides, citrates, edisylates, ethane disulphonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulphonates, mesylates, methylbromides, methylnitrates, methylsulphates, mucates, napsylates, nitrates, oxalates, pamoates, pantothenates, phenyl acetates, phosphates/diphosphates, polygalacturonates, propionates, salicylates, stearates, subacetates, succinates, sulphamides, sulphates, tannates, tartrates, teoclates, toluenesulphonates, triethiodides, ammonium, benzathines, chloroprocaines, cholines, diethanolamines, ethylenediamines, meglumines and procaines.

Further pharmaceutically acceptable salts can be formed with cations from metals like to aluminium, calcium, lithium, magnesium, potassium, sodium, zinc and the like (also see Pharmaceutical salts, Birge, S. M. et al., J. Pharm. Sci., (1977), 66, 1-19).

The pharmaceutically acceptable salts of the present invention can be synthesised from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoroacetates), also comprise a part of the invention.

Some abbreviated notations and their structure correspondences are listed below:

In a representation such as for example

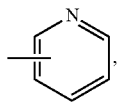

the solid line means that the ring system may be attached to the molecule via the carbon atom 1, 2 or 3, and is thus equivalent to the following representation

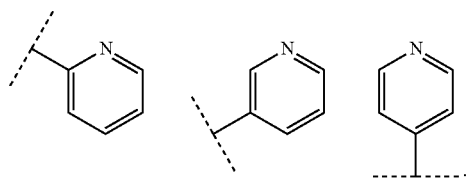

| List of abbreviations | |
|---|---|
| Ac | Acetyl |
| ACN | Acetonitrile |
| aq | Aqueous |
| ATP | adenosine triphosphate |
| Bn | Benzyl |
| Bu | Butyl |
| Boc | tert-butyloxycarbonyl |
| cat | Catalyst |
| conc | concentrated |
| d | day(s) |
| TLC | thin layer chromatography |
| DIEA | N,N-diisopropylethylamine |
| DMAP | 4-N,N-dimethylaminopyridine |
| DME | 1,2-dimethoxyethane |
| DMF | N,N-dimethylformamide |
| DMSO | Dimethylsulphoxide |
| dppf | 1.1'-bis(diphenylphosphino)ferrocene |
| EDC | 1-Ethyl-3-(3-dimethylaminopropyl)carbodiimide |
| ESI | electron spray ionization |
| Et | Ethyl |
| Et$_2$O | diethyl ether |
| EtOAc | ethyl acetate |
| EtOH | Ethanol |
| h | hour(s) |
| HATU | O-(7-azabenzotriazol-1-yl)-N,N,N',N'-tetramethyl-uronium hexafluorophosphate |
| Hep | Heptane |
| HPLC | high performance liquid chromatography |
| i | Iso |
| LC | liquid chromatography |
| LiHMDS | lithium bis(trimethylsilyl)amide |
| sln. | Solution |
| mCPBA | 3-Chloroperoxbenzoic acid |
| Me | Methyl |
| MeOH | Methanol |
| min | Minutes |
| MPLC | medium pressure liquid chromatography |
| MS | mass spectrometry |
| NBS | N-bromo-succinimide |
| NIS | N-iodo-succinimide |
| NMM | N-methylmorpholine |
| NMP | N-methylpyrrolidone |
| NP | normal phase |
| n.a. | not available |
| PBS | phosphate-buffered saline |
| Ph | Phenyl |
| Pr | Propyl |
| Pyr | Pyridine |
| rac | Racemic |
| Rf (R$_f$) | retention factor |
| RP | reversed phase |
| RT | Retention time (HPLC) |
| rt | ambient temperature |
| TBAF | tetrabutylammonium fluoride |
| TBDMS | tert-butyldimethylsilyl |
| TBME | tert-butylmethylether |
| TBTU | O-(benzotriazol-1-yl)-N,N,N',N'-tetramethyl-uronium tetrafluoroborate |
| tBu | tert-butyl |
| TEA | Triethylamine |
| temp. | Temperature |
| tert | Tertiary |
| Tf | Triflate |
| TFA | trifluoroacetic acid |
| THF | Tetrahydrofuran |
| TMS | Trimethylsilyl |
| TRIS | tris(hydroxymethyl)-aminomethane |
| Ts | p-Tosyl |
| TsOH | p-toluenesulphonic acid |
| UV | Ultraviolet |

By a therapeutically effective amount for the purposes of this invention is meant a quantity of substance that is capable of obviating symptoms of illness or alleviating these symptoms, or which prolong the survival of a treated patient.

Features and advantages of the present invention will become apparent from the following detailed examples which illustrate the fundamentals of the invention by way of example without restricting its scope:

Preparation of the Compounds According to the Invention

Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Intermediates and products may be purified by chromatography on silica gel, recrystallization and/or reverse phase HPLC(RHPLC). Discrete enantiomers may be obtained by resolution of racemic products using chiral HPLC. RHPLC purification methods used anywhere from 0-100% acetonitrile in water containing 0.1% formic acid or 0.1% TFA and used one of the following columns.

a) Waters Sunfire OBD C18 5 μm 30×150 mm column
b) Waters XBridge OBD C18 5 μm 30×150 mm column
c) Waters ODB C8 5 μm 19×150 mm column
d) Waters Atlantis ODB C18 5 μm 19×50 mm column.
e) Waters Atlantis T3 OBD 5 μm 30×100 mm column
f) Phenomenex Gemini Axia C18 5 μm 30×100 mm column HPLC Methods:
Analytical LC/MS Analysis Method A:
Column: Thermo Scientific, Aquasil C18, 50×2.1 mm, 5 μm column
Gradient:

| Time (min) | 0.1% Formic Acid in Water | 0.1% Formic Acid in CAN | Flow (ml/min) |
|---|---|---|---|
| 0 | 90 | 10 | 0.5 |
| 0.5 | 90 | 10 | 0.5 |
| 1.5 | 1 | 99 | 0.5 |
| 2.5 | 1 | 99 | 0.5 |
| 3.3 | 90 | 10 | 0.5 |
| 4.0 | 90 | 10 | 0.5 |

Analytical LC/MS Analysis Method B:
Column: Waters BEH 2.1×50 mm C18 1.7 μm column
Gradient:

| Time (min) | 95% Water/ 5% ACN (0.05% TFA) | ACN (0.05% TFA) | Flow (ml/min) |
|---|---|---|---|
| 0 | 90 | 10 | 0.8 |
| 1.19 | 0 | 100 | 0.8 |
| 1.7 | 0 | 100 | 0.8 |

General Synthetic Methods

Compounds of formula I may be prepared as shown in General Scheme Ia below.

Scheme Ia:

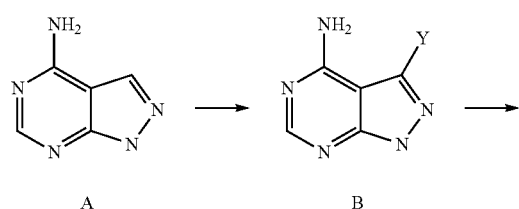

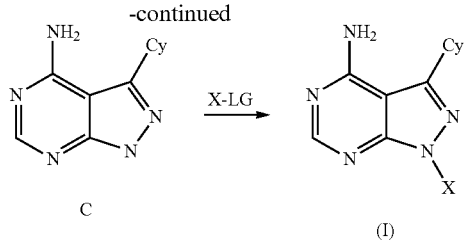

In Scheme Ia, A is reacted with suitable reagent to afford B (Y is OTf, Cl, Br, I), C can be prepared from B using an appropriate boronic acid or pinacol ester, in the presence of a suitable palladium catalyst system, for example bis(diphenylphosphino)ferrocene palladium (II) chloride complex or tetrakis(triphenylphosphine)palladium (0) in the prescence of an inorganic base like potassium carbonate, cesium carbonate or potassium phosphate in a suitable solvent system like combination of dioxane and water. X-LG (LG is a leaving group) is treated with suitable base and reacted with C to afford the compound of general formula (I).

Scheme Ib:

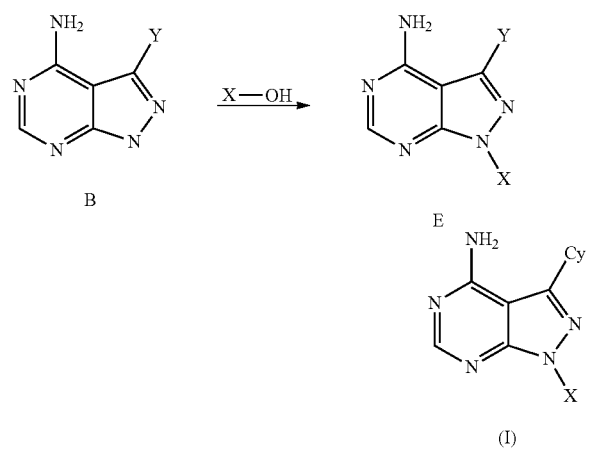

In Scheme Ib, B is reacted with alcohol contained X—OH in the presence of triphenylphosphine and suitable reagent for example DEAD, DIAD or DBAD in a suitable solvent like THF or toluene to afford E. E is then reacted with an appropriate boronic acid or pinacol ester, in the presence of a suitable palladium catalyst system, for example bis(diphenylphosphino)ferrocene palladium (II) chloride complex or to tetrakis(triphenylphosphine)palladium (0) in the prescence of an inorganic base like potassium carbonate, cesium carbonate or potassium phosphate in a suitable solvent system like combination of dioxane and water to afford the compound of general formula (I).

Method 1

Synthesis of Intermediate I-1

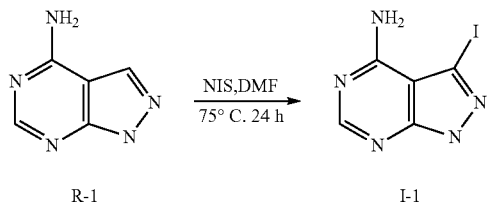

To a solution of R-1 (50.0 g, 0.37 mol) in DMF (350.0 mL) NIS (83.3 g, 0.37 mol) is added. The reaction mixture is heated to 75° C. for 24 h. The mixture is then cooled to room temperature and poured into water. The mixture is filtered and the percipitate is washed with water, dried under reduced pressure to afford compound I-1 (45.0 g, 48%).

Method 2

Synthesis of Intermediate 1-2

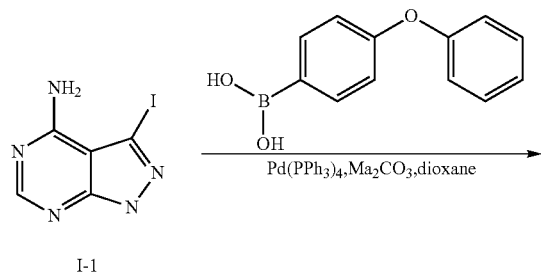

I-1

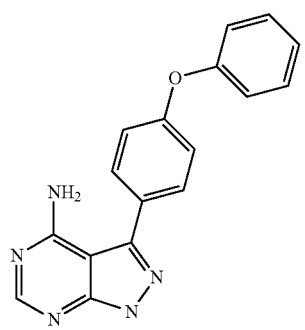

I-2

To a stirred solution of 1-1 (7.0 g, 26.8 mmol) in 1,4-dioxane (650.0 mL)/water (100.0 mL) (4-phenoxyphenyl)boronic acid (7.4 g, 34.6 mmol), tetrakis(triphenylphosphine)palladium(0) (0.93 g, 0.85 mmol) and Na$_2$CO$_3$ (5.6 g, 52.8 mmol) is added. The reaction mixture is heated to 90° C. for 60 hours, and then cooled to room temperature, and concentrated in vacuo. The residue is purifed via Combi-flash chromatography on silica gel to afford 1-2 (3.5 g, 43.0%).

Method 3

Synthesis of Intermediate 1-3

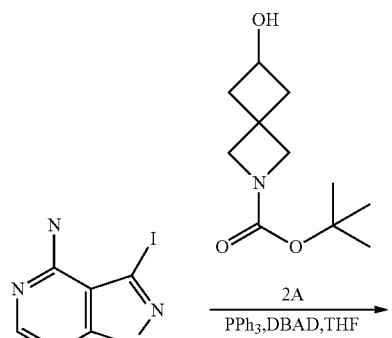

I-1

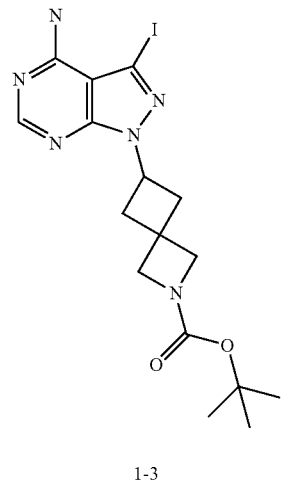

1-3

To a mixed solution of 1-1 (5.0 g, 0.019 mol), compound 2A (4.1 g, 0.019 mol), Ph$_3$P (6.0 g, 0.023 mol) in THF (50.0 mL) DBAD (4.6 g, 0.023 mol) is added dropwise under nitrogen at room temperature. The reaction mixture is heated to 60° C. after addition and stirred overnight. The reaction mixture is cooled to room temperature and concentrated in vacuo. The residue is purified via Combi-flash chromatography on silica gel then via prep-HPLC to afford compound 1-3 (2.8 g, 33%).

Method 4

Synthesis of Intermediate 1-8

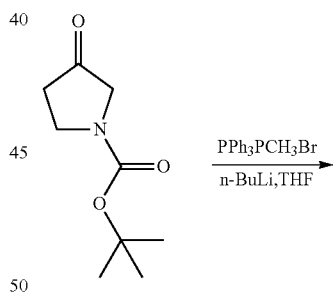

R-2

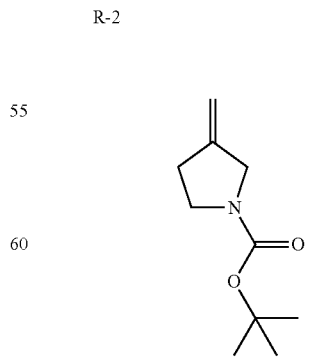

I-4

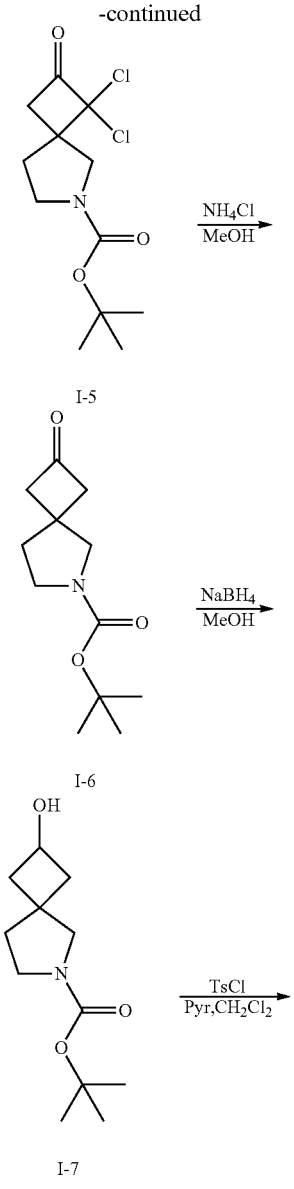

with brine, dried with Na₂SO₄, concentrated and purified by flash chromatography (SiO₂, Hep to 25% EtOAc in Hep) to give compound 1-4 (70 g, 36%).

To a solution of 1-4 (20 g, 109 mmol) in Et₂O (150 mL) is added Zn—Cu (56.2 g, 436 mmol) at 10° C. under N₂. Trichloroacetyl chloride (39.7 g, 218 mmol) in DME (150 mL) is added. The mixture is allowed to warm to ambient temperature and stirred for 2 days. The mixture is treated with aqueous NaHCO₃ and extracted with EtOAc. The organic layers are washed with brine, dried with Na₂SO₄, concentrated and purified by flash chromatography (SiO₂, Hep to 25% EtOAc in Hep) to give 1-5 (11 g, 34%).

To a solution of 1-5 (35.5 g, 121 mmol) in saturated NH₄Cl (64.7 g, 1.21 mol) in MeOH (400 mL) is added Zn (79.1 g, 1.21 mol). The mixture is stirred at ambient temperature for 8 h. The mixture is treated with H₂O and extracted with EtOAc. The organic layers are washed with brine, dried with Na₂SO₄, concentrated and purified by flash chromatography (SiO₂, Hep to 25% EtOAc in Hep) to afford 1-6 (19 g, 69%).

To the mixture of 1-6 (19 g, 84.3 mmol) in THF (200 mL) is added NaBH₄ (12.8 g, 337.2 mmol) at 0° C. and then stirred at ambient temperature for 6 h. The mixture is treated with MeOH and H₂O, then extracted with EtOAc. The organic layers are washed with brine, dried with Na₂SO₄, concentrated and purified by flash chromatography (SiO₂, Hep to 50% EtOAc in Hep) to yield 1-7 (12 g, 63%).

To the mixture of 1-7 (22 g, 96.8 mmol) and pyridine (23.2 g, 290.4 mmol) in CH₂Cl₂ (300 mL) is added TsCl (27.7 g, 145.2 mmol) at 0° C. and then stirred at ambient temperature overnight. The mixture is treated with H₂O and extracted with EtOAc. The organic layers are washed with brine, dried with Na₂SO₄, concentrated and purified by flash chromatography (SiO₂, Hep to 40% EtOAc in Hep) to afford 1-8 (26.6 g, 72%) m/z 382.2 [M+1-1].

Method 5

Synthesis of Intermediate 1-9 and Seperation of Disastereomers I-10 and I-11

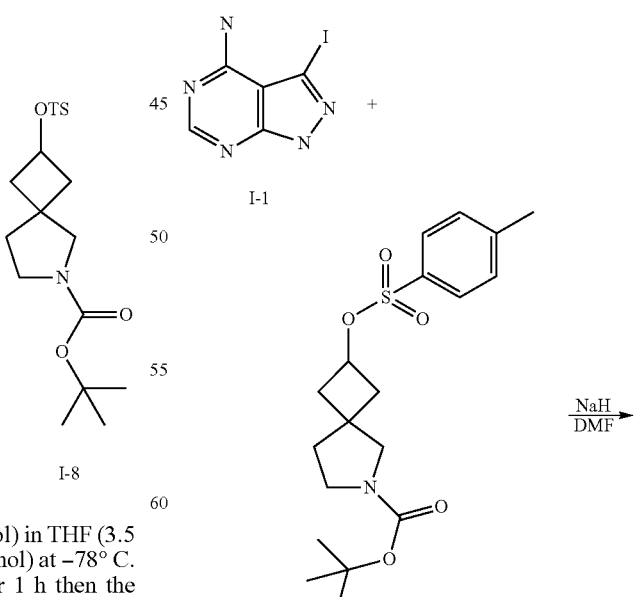

To a solution of PPh₃CH₃Br (578 g, 1.62 mol) in THF (3.5 L) is added a solution of n-Buli (600 mL, 1.5 mol) at −78° C. under N₂. The mixture is stirred at 0° C. for 1 h then the solution of R-2 (200 g, 1.08 mol) in THF (2.0 L) is added to the reaction mixture at 0° C. The mixture is allowed to warm to ambient temperature, stirred for 1 h, then poured into H₂O and extracted with EtOAc. The organic layers are washed

Method 6

Synthesis of Intermediate 1-12

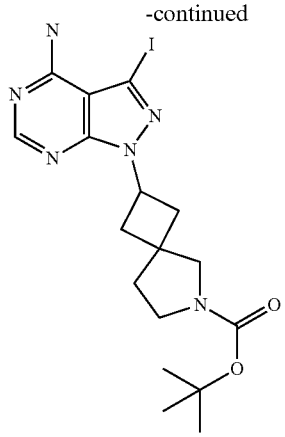

I-9

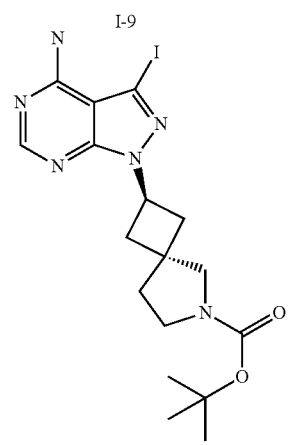

I-10

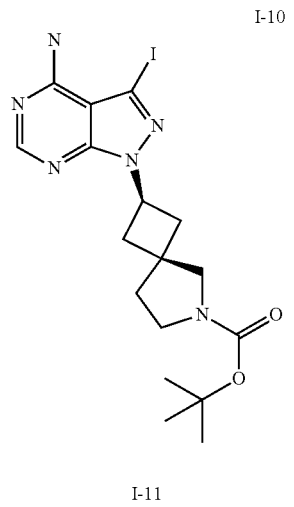

I-11

To a stirred solution of 1-1 (1.0 g, 3.83 mmol) in DMF (5 mL) sodium hydride (0.17 g, 4.2 mmol) is added. After 5 min, 1-8 (1.6 g, 4.2 mmol) is added and the reaction mixture is heated to 70° C. for 2 days. The reaction is cooled to room temperature and diluted with saturated NH$_4$Cl solution (100 mL). The organics are extracted with ethyl acetate (4×250 mL), washed with brine, dried over sodium sulfate and concentrated in vacuo. The residue is purified via Combi-flash column on silica gel (0-8% MeOH in DCM) to afford 1-9 (1.75 g, 97.1%) m/z 472.28 [M+1-1], RT 0.72. 1-9 is seperated by prep-HPLC to afford diastereomers I-10 (1.6 g, 88.8%) m/z 472.28 [M+1-1], RT 0.98; I-11 (0.15 g, 8.3%) m/z 472.54 [M+H], RT 0.69.

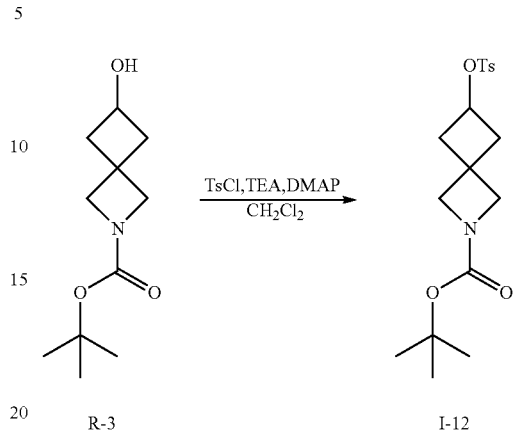

A solution of R-3 (5.0 g, 23 mmol) in CH$_2$Cl$_2$ is treated with TEA (6.5 mL, 47 mmol) and DMAP (0.57 g, 4.7 mmol). The mixture is stirred for 24 h then concentrated in vacuo. The resiude is dissolved in EtOAc and washed with saturated aquoues ammonium chloride and brine. The organics are collected and volatiles are removed in vacuo. The crude resiude is triturated with Et$_2$O and solid filtered and collected to afford 1-12 (5.6 g, 65%) m/z 367.9 [M+].

Method 7

Synthesis of Intermediate 1-13

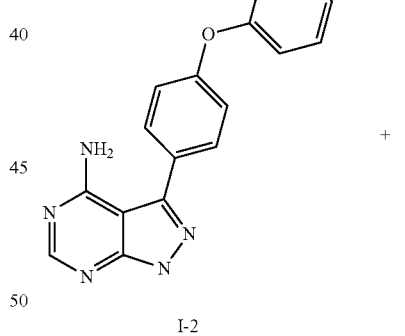

I-2

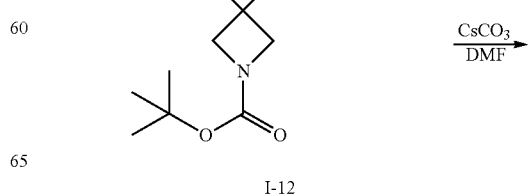

I-12

Method 8

Synthesis of Intermediate 1-15

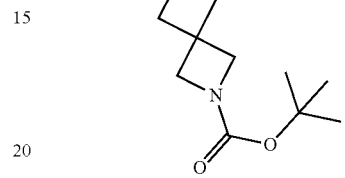

1-3

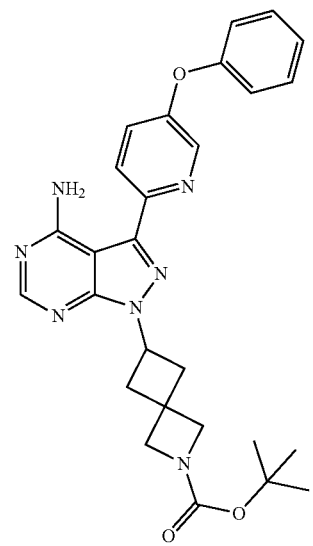

I-15

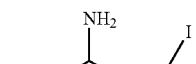

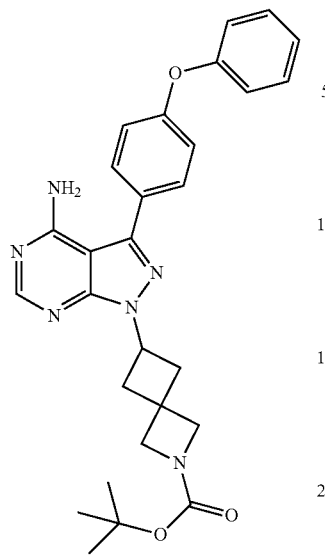

I-13

To a stirred solution of 1-2 (0.15 g, 0.5 mmol) in DMF (3.0 mL) 1-12 (0.2 g, 0.54 mmol) and $Cs_2CO_3$ (0.32 g, 1.0 mmol) is added. The reaction mixture is heated to 60° C. After 18 hours, the reaction mixture is concentrated in vacuo and purified via Combi-flash chromatography on silica gel (using a solvent gradient of 5% MeOH in $CH_2Cl_2$) to afford 1-13 (0.18 g, 73%). The following intermediate was prepared in similar fashion:

| Structure | Intermediate | m/z |
|---|---|---|
| 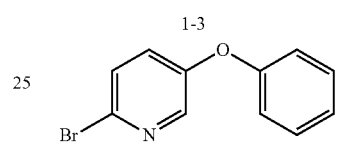 | I-14 | 513.2 (1.08) |

In a microwave reactor is charged 1-3 (0.35 g, 0.77 mmol), tetrakis (triphenylphosphine)palladium (0) (0.09 g, 0.077 mmol), hexamethyldistannane (0.19 mL, 0.92 mmol) in 1,4-dioxane (0.2 mL). The reaction mixture is degassed with argon for 5 min and then is heated to 115° C. for 1 hour. The reaction mixture is cooled to room temperature and followed by the addition of R-4 (0.60 g, 1.84 mmol) and tetrakis(triphenylphosphine)palladium (0) (0.09 g, 0.077 mmol). The reaction mixture is degassed with argon for 5 min and then heated to 115° C. overnight. The reaction mixture is cooled to room temperature and concentrated in vacuo. The residue is purified via Combi-flash chromatography on silica gel (using a solvent gradient of 0-6% MeOH in $CH_2Cl_2$) to afford 1-15 (0.27 g, 70.7%).

The following intermediates were prepared in similar fashion:

| Structure | Intermediate | m/z |
|---|---|---|
| 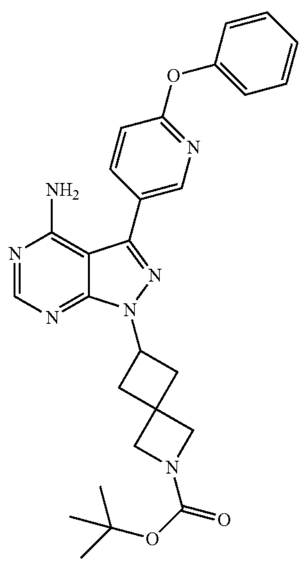 [SMILES: CC(C)(C)OC(=O)N1CC2(CC(n3nc(-c4ccc(Oc5ccccc5)nc4)c4c(N)ncnc43)C2)C1] | I-16 | |
| 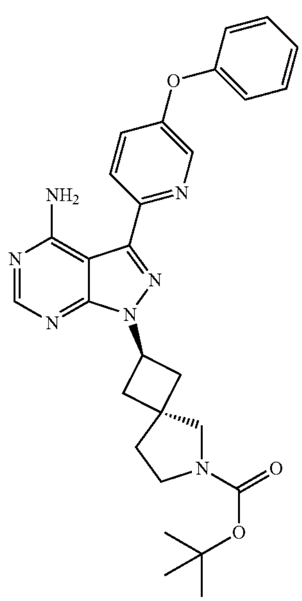 [SMILES: CC(C)(C)OC(=O)N1CC[C@]2(C1)C[C@H](n1nc(-c3ccc(Oc4ccccc4)cn3)c3c(N)ncnc31)C2] | I-17 | 515.82 (1.19) |
| | I-18 | 515.93 (1.08) |
| | I-19 | 623.39 (2.38) |

Method 9

Synthesis of Example 1

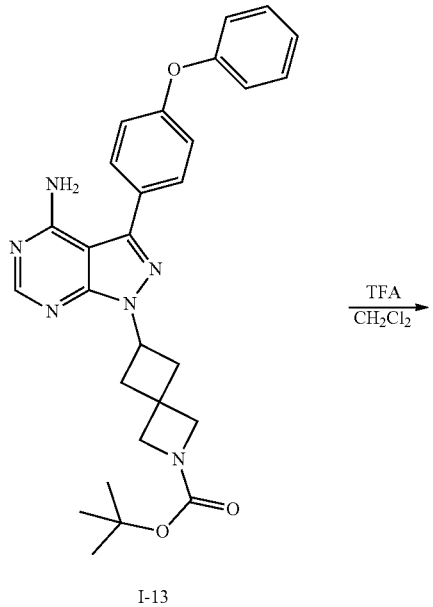

I-13

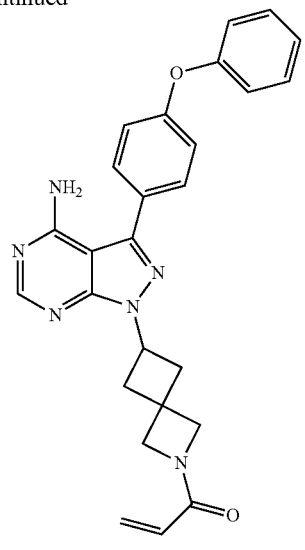

Ex 1

To a stirred solution of R-13 (0.18 g, 0.36 mmol) in CH$_2$Cl$_2$ (5.0 mL) TFA (0.21 g, 1.8 mmol) is added at room temperature. After 3 hours, the reaction mixture is pardoned between 10% MeOH in CH$_2$Cl$_2$ and saturated aqueous NaHCO$_3$. The organics are collected, dried over MgSO$_4$, filtered and concentrated in vacuo to afford 1-20 (0.12 g, 83.4%).

To a stirred solution of 1-20 (0.039 g, 0.098 mmol) in DMF (2.0 mL) acrylic acid (0.007 mL, 0.098 mmol), TBTU (31.4 mg, 0.098 mmol) and DIPEA (0.043 mL, 0.25 mmol) is added at room temperature. After 15 min, the reaction solution is concentrated in vacuo.

The residue is purified via Combi-flash chromatography on silica gel (using a solvent gradient of 5% MeOH in CH$_2$Cl$_2$) to afford Ex 1 (0.014 g, 31.6%) m/z 453.0 [M+1-1], RT 0.80 min The following compounds were prepared in similar fashion:

Ex 2, 3, 4, 5

Method 10

Synthesis of Example 11

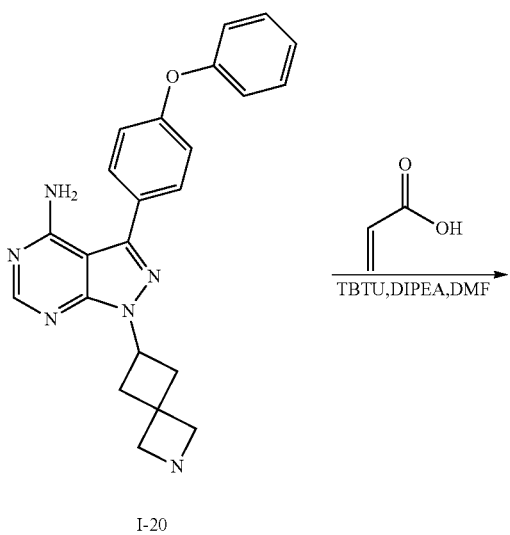

I-20

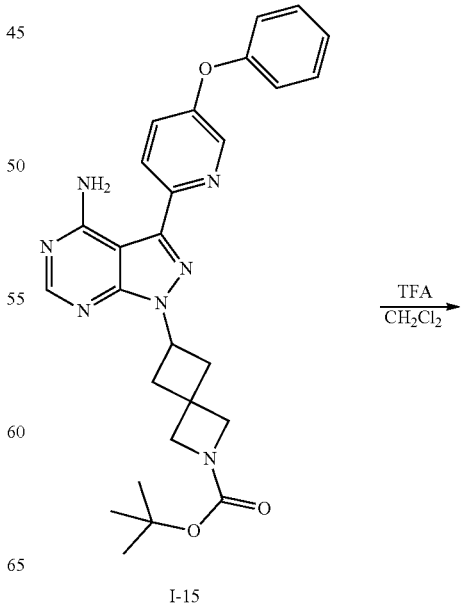

I-15

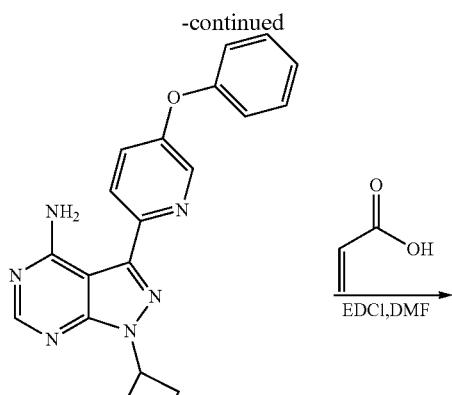

I-21

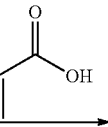

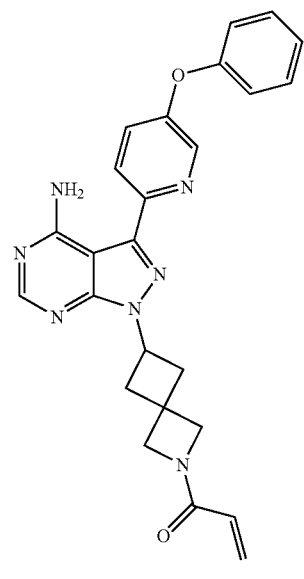

Ex 11

To a stirred solution of 1-15 (0.27 g, 0.54 mmol) in CH$_2$Cl$_2$ TFA (1.5 g, 13.1 mmol) is added at room temperature. After 1 hour, the reaction mixture is concentrated in vacuo. The residue is passed through NaHCO$_3$-containing column to afford 1-21 (0.21 g, 96.9%).

To a stirred solution of acrylic acid (0.014 g, 0.19 mmol) in DMF (2.0 mL) EDCI (0.04 g, 0.2 mmol) is added at room temperature. After 5 min, 1-21 (0.07 g, 0.18 mmol) is added to the reaction mixture. After 14 hours, the reaction is quenched with saturated aqueous NH$_4$Cl (4.0 mL). The organic is extracted with ethyl acetate and washed with brine, dried over sodium sulfate and concentrated in vacuo. The residue is purified via HPLC to afford Ex 11 (0.017 g, 21.4%) m/z 455.55 [M+], RT 0.87 min The following compounds were prepared in similar fashion:
Ex 6, 7, 8, 9, 10, 12, 13, 14, 15, 16, 17

Description of Biological Properties

BTK Assay

An HTRF assay (Cisbio KinEASE-TK cat #62TKOPEC) was performed to quantitate the ability of test compounds to inhibit BTK mediated phosphorylation of substrate. Assays were assembled in 384 well plates where 6 nM of full-length human His-tagged BTK (Life Technologies cat #PV3587) and test compound at varying concentrations were preincubated for 15 minutes at 28° C. Then, 1 uM of TK substrate-biotin and 30 uM ATP were added and incubated for an additional 30 minutes at 28° C. Phosphorylation was detected by adding 62.5 nM Streptavidin-XL665 and TK-Antibody Cryptate diluted 1:100 in HTRF detection buffer (Cisbio cat #62SDBRDF) and incubated for 60 minutes at RT. The plate was read on an Envision plate reader and the fluorescence is measured at 620 nm (cryptate) and 665 nm (XL665). A ratio is calculated (665/620) and converted to POC relative to control and blank wells.

Assay Buffer:

50 mM HEPES (Invitrogen #15630), 0.01% Brij-35 (sigma #B4184), 10 mM MgC12 (Sigma M1028), 1 mM EGTA (Ambion AM9262) and 100 uM sodium orthovanedate (Sigma S6508), 1 mM DTT (Sigma D5545) and 10 nM supplement enzyme buffer (Cisbio cat#61SEBALB).

Therapeutic Use

On the basis of their biological properties the compounds of formula (I) according to the invention, or their tautomers, racemates, enantiomers, diastereomers, mixtures thereof and the salts of all the above-mentioned forms are suitable for treating autoimmune and allergic disorders in that they exhibit good inhibitory effect upon BTK.

Such diseases include for example: rheumatoid arthritis, systemic lupus erythromatosis, scleroderma, asthma, allergic rhinitis, allergic eczema, B cell lymphoma, multiple sclerosis, juvenile rheumatoid arthritis, juvenile idiopathic arthritis, inflammatory bowel disease, graft versus host disease, psoriatic arthritis, ankylosing spondylitis and uveitis.

The compounds of formula (I) may be used on their own or in combination with other active substances according to the invention, optionally also in combination with other pharmacologically active substances.

Suitable preparations include for example tablets, capsules, suppositories, solutions—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may of course contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

All patent and non-patent documents or literature cited in this application are herein incorporated by reference in their entirety.

The invention claimed is:

1. A compound of the formula (I)

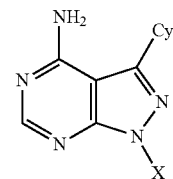

wherein:

Cy is carbocycle, heteroaryl or heterocycle, each is substituted by $R_1$ and optionally substituted by halogen, halo $C_{1-4}$ alkyl, $C_{1-4}$ alkyl, oxo and $C_{1-4}$ alkoxy;

$R_1$ is chosen from:

L-Ar, $C_{1-6}$ alkyl, —S(O)$_m$—$R_3$ and $C_{1-6}$ alkoxy, each Ar, $C_{1-6}$ alkyl and $C_{1-6}$ alkoxy are optionally substituted by benzyl, halogen, halo $C_{1-4}$ alkyl, $C_{1-4}$ alkyl, $R_2$—S(O)$_m$—, —CN, —C(O)—N($R_3$)$_2$ or $C_{1-4}$ alkoxy;

L is a linker chosen from a bond, O, >C(O), —(CH$_2$)$_n$—, —O—(CH$_2$)$_n$—, —N($R_3$)—, —N($R_3$)—(CH$_2$)$_n$—, —(CH$_2$)$_n$—N($R_3$)—, —C(O)—N($R_3$)—, —C(O)—N($R_3$)—(CH$_2$)$_n$—, —N($R_3$)—C(O)—N($R_3$)—, —N($R_3$)—C(O)—, —S(O)$_m$—N($R_3$)—, $R_3$—S(O)$_m$—, and —N($R_3$)—S(O)$_m$—, wherein the —CH$_2$— in each L can have 1-2 hydrogens replaced by $C_{1-3}$ alkyl, said $C_{1-3}$ alkyl groups can optionally cyclize to form a $C_{3-6}$ cycloalkyl ring;

Ar is carbocycle, heterocycle or heteroaryl;

X of the formula (I) is

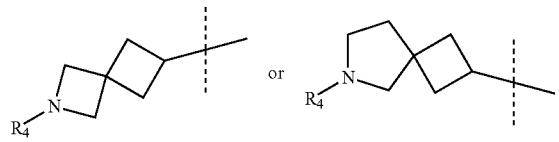

each X is optionally substituted by halogen, halo $C_{1-4}$ alkyl, $C_{1-4}$ alkyl and $C_{1-4}$ alkoxy;

$R_4$ is

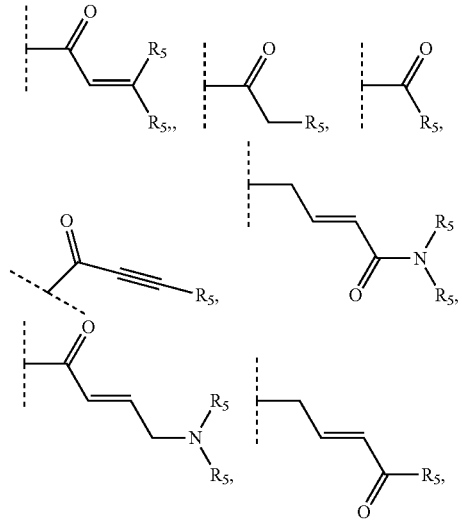

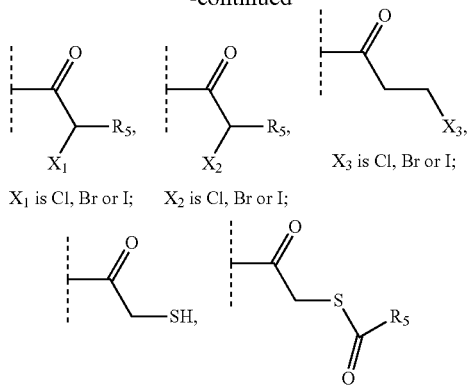

$X_1$ is Cl, Br or I;   $X_2$ is Cl, Br or I;   $X_3$ is Cl, Br or I;

each n is independently 1-4;
each m is independently 0-2;
each $R_2$ and $R_3$ are independently chosen from hydrogen or $C_{1-4}$ alkyl;
each $R_5$ is independently chosen from hydrogen, halogen, $C_{1-4}$ alkyl, $C_{1-4}$ alkoxy, $C_{1-4}$ alkyl$C_{1-4}$alkoxy, $C_{1-4}$ alkylhydroxy, —$(CH_2)_n$-heterocycle and heterocycle each heterocycle optionally substituted by halogen, OH or $R_2$—$S(O)_m$—;
each group defined above for Cy, $R_1$-$R_5$, and Y can be, where possible partially or fully halogenated;
or a pharmaceutically acceptable salt thereof.

2. The compound according to claim 1 wherein
Cy is phenyl, pyrazolyl, pyridinyl, pyrrolyl, imidazolyl, thiazolyl, furanyl, oxazolyl, isoxazolyl, thienyl, pyridazinyl, pyrimidinyl, pyrazinyl or pyranyl each is substituted by $R_1$ and optionally substituted by $C_{1-4}$ alkyl, F, Cl or oxo;
$R_1$ is chosen from:
L-Ar and —$S(O)_m$—$R_3$, each $R_1$ is optionally substituted by Br, $C_{1-4}$ alkyl, $R_3$—$S(O)_2$—, —CN, —C(O)—NH($R_3$) and $C_{1-3}$ alkoxy;
Ar is phenyl, pyridinyl, pyridazinyl, pyrimidinyl optionally substituted by benzyl, pyrazinyl, benzoxazolyl, indolyl, isoindolyl, benzofuranyl, benzimidazolyl, benzothiazolyl, piperidinyl, piperazinyl or pyrrolidinyl
or a pharmaceutically acceptable salt thereof.

3. The compound according to claim 2 wherein
Cy is phenyl or pyridinyl, each is substituted by $R_1$ and optionally substituted by F, Cl, oxo or $C_{1-2}$ alkoxy;
$R_1$ is L-Ar, each $R_1$ is optionally substituted by Br, $C_{1-4}$ alkyl, $CH_3$—$S(O)_2$—, —CN, —C(O)—NH($R_3$) and $C_{1-2}$ alkoxy;
Ar is phenyl, pyridinyl, pyridazinyl, pyrimidinyl optionally substituted by benzyl, pyrazinyl, benzoxazolyl, indolyl, isoindolyl, benzofuranyl, benzimidazolyl, benzothiazolyl or piperidinyl;
or a pharmaceutically acceptable salt thereof.

4. The compound according to claim 3 wherein
Cy is phenyl or pyridinyl, each is substituted by $R_1$ and optionally substituted by F, Cl, oxo or $C_{1-2}$ alkoxy;
L-Ar is optionally substituted by F, Cl, $C_{1-4}$ alkyl, $CH_3$—$S(O)_2$—, —CN, —C(O)—NH($CH_3$) and $C_{1-2}$ alkoxy;
Ar is phenyl or pyrimidinyl;
or a pharmaceutically acceptable salt thereof.

5. The compound according to claim 4 wherein
X is

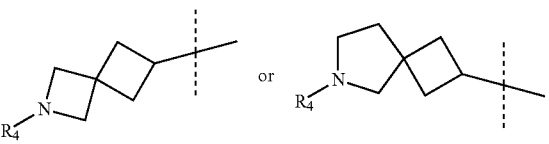

or a pharmaceutically acceptable salt thereof.

6. The compound according to claim 5 wherein
$R_4$ is

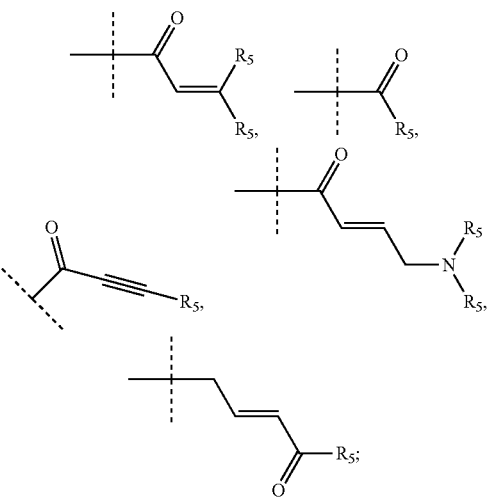

each $R_5$ is independently chosen from hydrogen, $C_{1-3}$ alkyl, halo $C_{1-3}$ alkyl, $C_{1-3}$ alkyl$C_{1-3}$ alkoxy, —$CH_2$-heterocycle and heterocycle each heterocycle optionally substituted by F, Cl, OH and $CH_3$—$S(O)_2$— and each heterocycle chosen from pyrrolidinyl, piperidinyl, morpholinyl, 1,4-oxazepane and oxirane;
or a pharmaceutically acceptable salt thereof.

7. The compound according to claim 6 wherein
Cy is

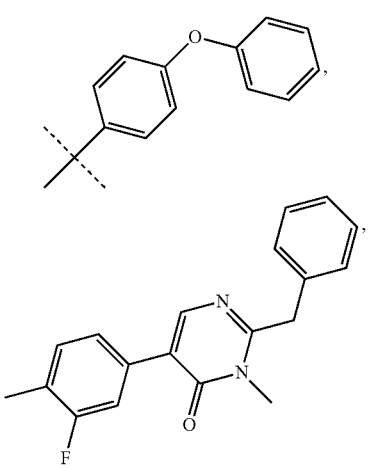

-continued
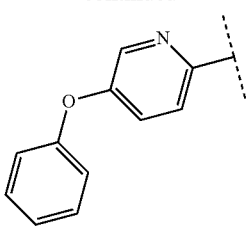
or
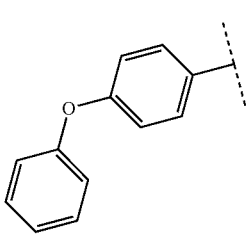
or a pharmaceutically acceptable salt thereof.
8. The compound according to claim 7 wherein X is
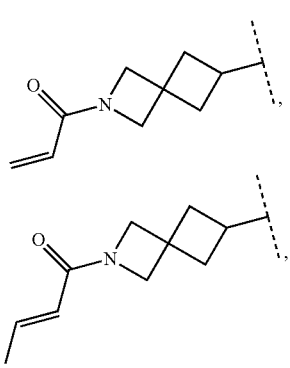
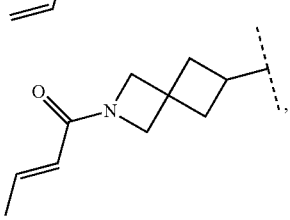
-continued
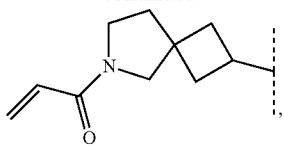
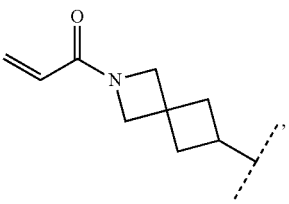
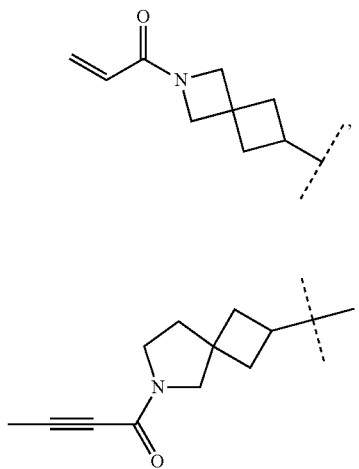
or
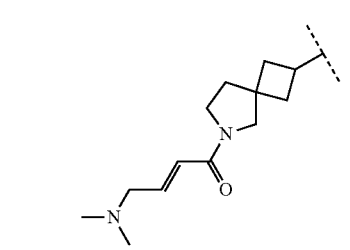
or a pharmaceutically acceptable salt thereof.
9. A compound chosen from
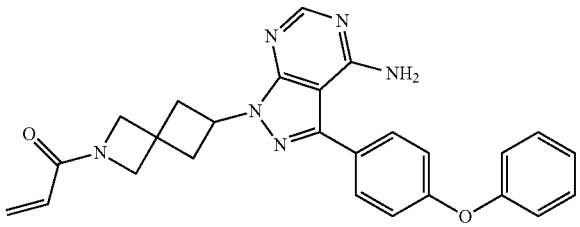

43
-continued
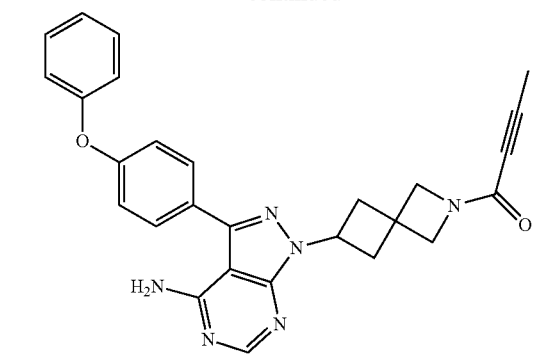
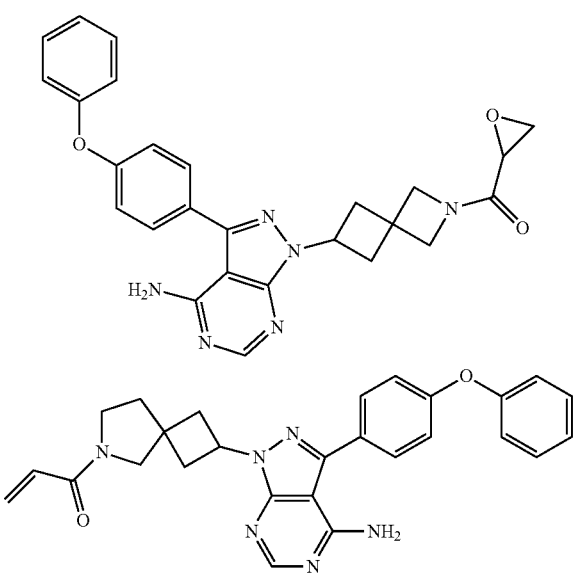
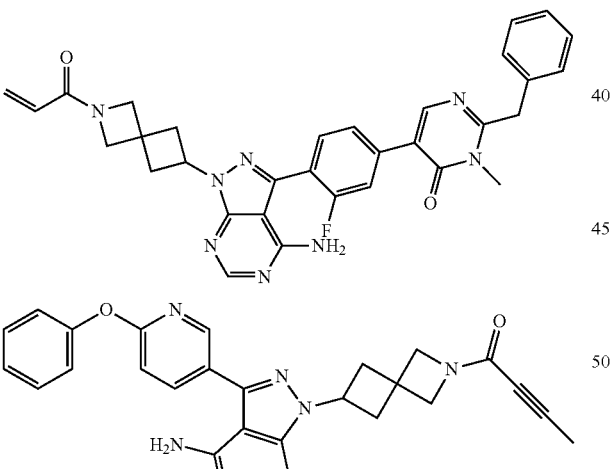
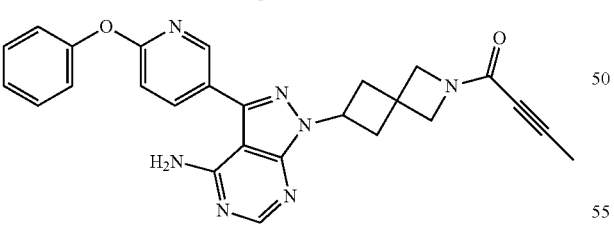
44
-continued
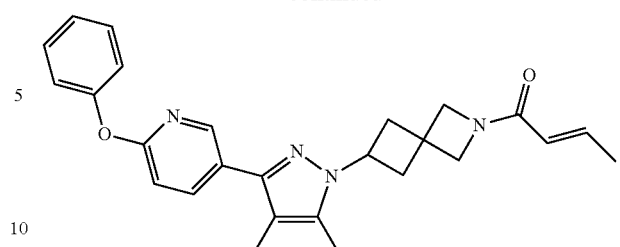
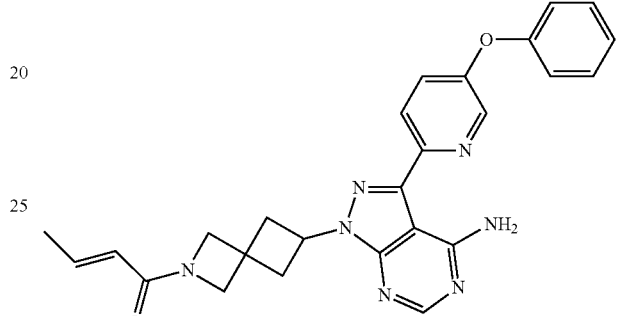
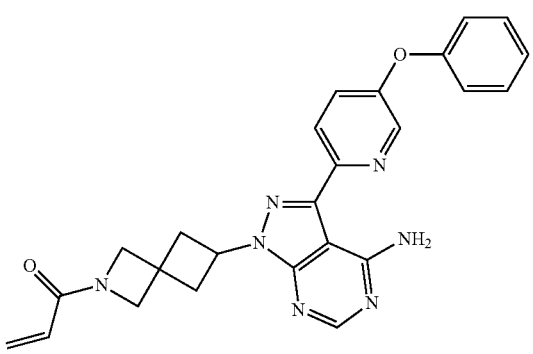
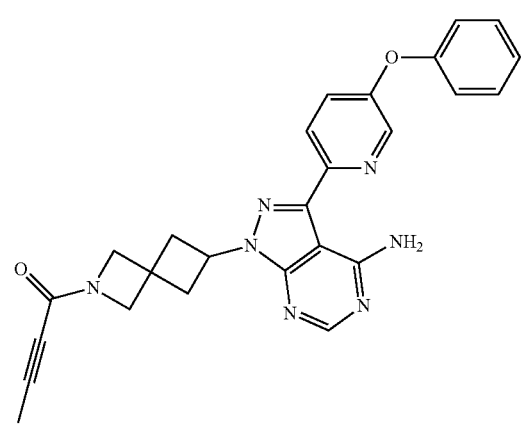

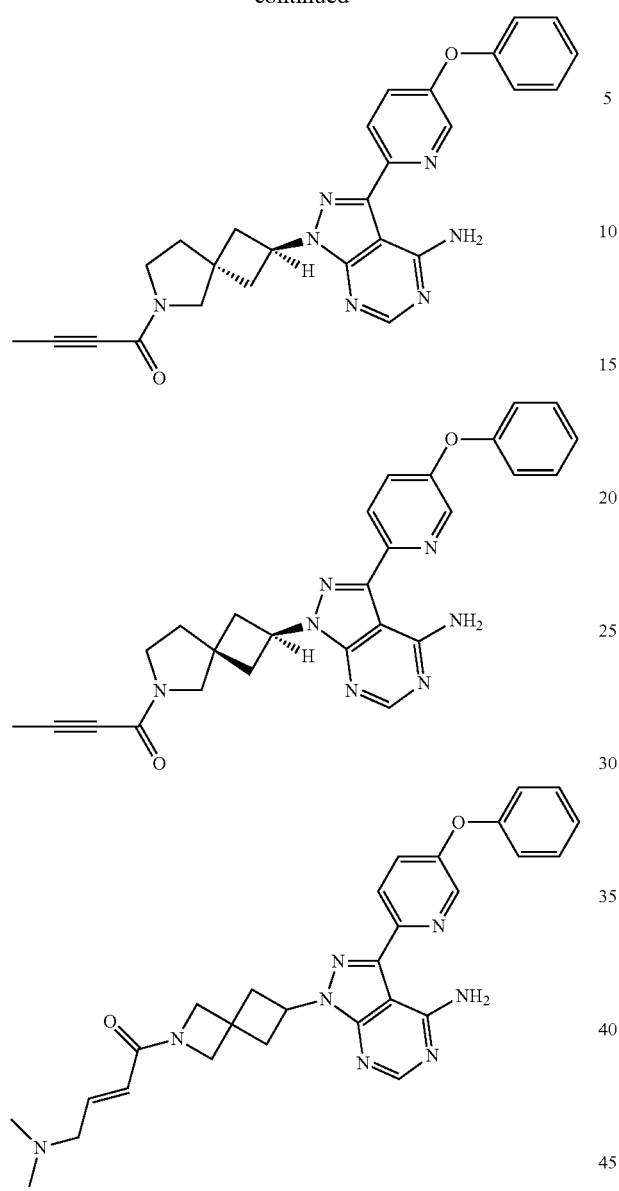
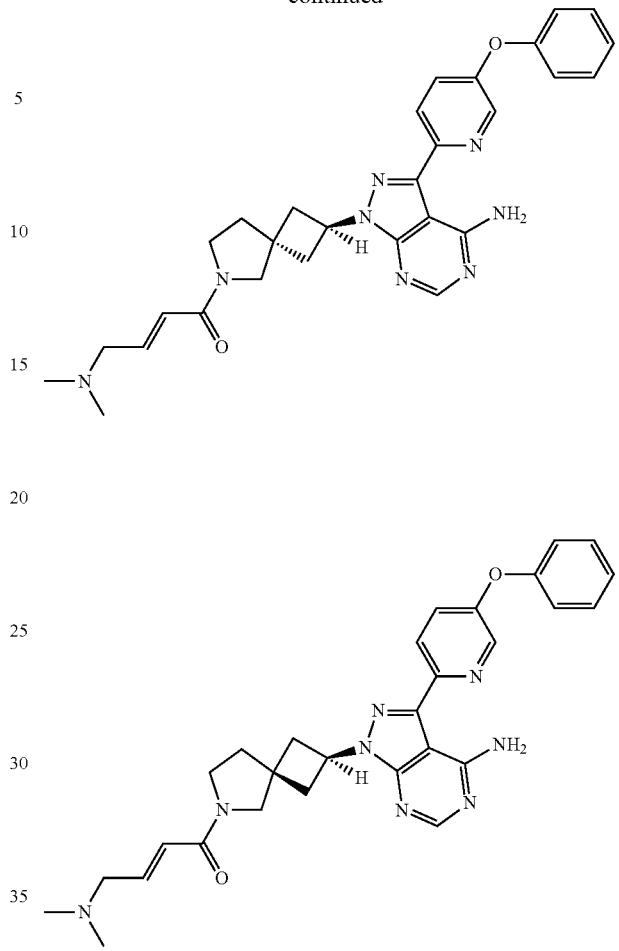
or a pharmaceutically acceptable salt thereof.
10. A pharmaceutical composition comprising a therapeutically effective amount of a compound according to claim 1 or a pharmaceutically acceptable salt thereof.
* * * * *